(12) United States Patent
Craig et al.

(10) Patent No.: US 7,224,825 B2
(45) Date of Patent: May 29, 2007

(54) DETECTING AND IDENTIFYING HAZARDOUS SUBSTANCES CONTAINED IN MAIL ARTICLES

(75) Inventors: William C. Craig, Endwell, NY (US); John Gofran, Endicott, NY (US); Rosemary D. Paradis, Vestal, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 831 days.

(21) Appl. No.: 10/417,570

(22) Filed: Apr. 17, 2003

(65) Prior Publication Data

US 2004/0010379 A1 Jan. 15, 2004

Related U.S. Application Data

(60) Provisional application No. 60/373,527, filed on Apr. 18, 2002.

(51) Int. Cl.
G06K 9/00 (2006.01)
G06K 9/62 (2006.01)
G06F 19/00 (2006.01)
G01N 15/02 (2006.01)
G01N 31/00 (2006.01)

(52) U.S. Cl. .............. 382/128; 382/224; 356/336; 702/29

(58) Field of Classification Search ............ 382/100, 382/128, 159, 181, 190, 224; 356/336, 338; 436/172; 702/19, 29
See application file for complete search history.

(56) References Cited

U.S. PATENT DOCUMENTS

| | | | |
|---|---|---|---|
| 4,071,298 A | 1/1978 | Falconer | |
| 4,264,206 A | 4/1981 | Hattori | |
| 4,548,500 A | 10/1985 | Wyatt et al. | |
| 4,661,913 A * | 4/1987 | Wu et al. | 702/19 |
| 4,847,198 A | 7/1989 | Nelson et al. | |
| 5,218,529 A | 6/1993 | Meyer et al. | |
| 5,254,861 A | 10/1993 | Carpenter et al. | |
| 5,393,979 A | 2/1995 | Hsi | |
| 5,424,959 A | 6/1995 | Reyes et al. | |
| 5,715,182 A | 2/1998 | Asai et al. | |
| 5,720,769 A * | 2/1998 | van Oort et al. | 607/17 |
| 5,721,613 A | 2/1998 | Linowski et al. | |
| 5,866,430 A | 2/1999 | Grow | |
| 5,891,656 A | 4/1999 | Zarling et al. | |
| 5,891,659 A | 4/1999 | Murakami et al. | |
| 5,895,922 A | 4/1999 | Ho | |
| 5,977,540 A | 11/1999 | Reents, Jr. | |

(Continued)

*Primary Examiner*—Matthew C. Bella
*Assistant Examiner*—Yubin Hung
(74) *Attorney, Agent, or Firm*—Tarolli, Sundheim, Covell & Tummino LLP (57) ABSTRACT

A method and computer program product are described for detecting and identifying airborne particular matter comprising a plurality of particles. The backscatter induced by each of the particles under a light source is measured to determine a backscatter value for each particle. The autofluorescence intensity of each of the particles around at least one characteristic wavelength is then measured to obtain at least one autofluorescence intensity value for each particle. The measured autofluorescence intensities and the backscatter values from the plurality of particles are processed to determine if a potential biohazard exists. At least one autofluorescence intensity value for each particle is provided to a pattern recognition classifier if a potential biohazard is present. The classifier is trained to recognize at least one variety of airborne particulate matter.

19 Claims, 6 Drawing Sheets

U.S. PATENT DOCUMENTS

| | | |
|---|---|---|
| 5,999,250 A | 12/1999 | Hairston et al. |
| 6,058,352 A | 5/2000 | Lu et al. |
| 6,091,843 A | 7/2000 | Horesh et al. |
| 6,142,025 A | 11/2000 | Zborowski et al. |
| 6,194,731 B1 | 2/2001 | Jeys et al. |
| 6,221,671 B1* | 4/2001 | Groner et al. ............... 436/63 |
| 6,272,376 B1 | 8/2001 | Marcu et al. |
| 6,272,479 B1 | 8/2001 | Farry et al. |
| 6,389,408 B1* | 5/2002 | Carrieri ...................... 706/48 |
| 6,606,157 B1* | 8/2003 | Kaye et al. ................. 356/336 |
| 6,885,440 B2* | 4/2005 | Silcott et al. ................ 356/73 |
| 6,887,710 B2* | 5/2005 | Call et al. .................... 436/53 |
| 2004/0048264 A1* | 3/2004 | Stoughton et al. ............ 435/6 |

* cited by examiner

```
                    ┌─────────┐
                    │  START  │─── 172
                    └────┬────┘
      170                │
                         ▼
                ┌─────────────────────┐
                │ OBTAIN AEROSOL SAMPLE │─── 174 ◄──┐
                └──────────┬──────────┘             │
                           ▼                        │
                ┌─────────────────────┐             │
                │   FILTER SAMPLE TO  │─── 176      │
                │ REMOVE LARGE PARTICLES │          │
                └──────────┬──────────┘             │
                           ▼                        │
                ┌─────────────────────┐             │
                │  MEASURE BACKSCATTER │─── 178     │
                └──────────┬──────────┘             │
                           ▼                        │
    ┌──────────────┐    ┌─────────────────────┐     │
    │  NORMALIZE   │    │      MEASURE        │     │
    │AUTOFLUORESCENCE│◄─ │   AUTOFLUORESCENCE  │─ 180│
    │   SIGNALS    │    │   INTENSITY VALUES  │     │
    └──────┬───────┘    └──────────┬──────────┘     │
       182 │                       ▼                │
           │                    ◇ 184               │
           │              DOES AN ALARM             │
           └────────────► CONDITION EXIST ? ────N───┘
                                │
                                Y
                                ▼
                ┌───────────────────────────────────┐
                │ PROVIDE AUTOFLUORESCENCE INTENSITY │─ 186
                │ VALUES TO A PATTERN RECOGNITION CLASSIFIER │
                └──────────────┬────────────────────┘
                               ▼
                ┌───────────────────────────────────┐
                │   IDENTIFY THE DETECTED           │─ 188
                │   SUBSTANCE AND REPORT RESULTS    │
                └──────────────┬────────────────────┘
                               ▼
                           ┌───────┐
                           │  END  │─── 190
                           └───────┘
```

Fig.10

DETECTING AND IDENTIFYING HAZARDOUS SUBSTANCES CONTAINED IN MAIL ARTICLES

This application claims the benefit of U.S. Provisional Application No. 60/373,527, filed Apr. 18, 2002.

BACKGROUND OF THE INVENTION

1. Technical Field

This invention relates generally to the detection and identification of hazardous material in a mail sorting facility, and, more particularly, to an integrated system to sense and characterize particulate matter within or on flat mail or letter mail articles.

2. Description of the Prior Art

There is an increased awareness of the potential for large-scale introduction of hazardous materials, either explosives or biological organisms, to create chaos in our society or harm innocent people. One potential delivery method terrorists or other criminals utilize to deliver these deadly materials is the mail.

As contaminated envelopes are processed through postal facilities, the mail handling equipment within the facility can become contaminated and postal operations personnel can be exposed to contamination. An effective system is needed to provide mail-handling operations at the postal facilities with the capability to detect and identify airborne particulate matter and alert mail processing personnel of a potentially hazardous condition.

SUMMARY OF THE INVENTION

To this end, in accordance with one aspect of the invention, a method is disclosed for detecting and identifying airborne particular matter comprising a plurality of particles. The backscatter induced by each of the particles under a light source is measured to determine a backscatter value for each particle. The autofluorescence intensity of each of the particles around at least one characteristic wavelength is then measured to obtain at least one autofluorescence intensity value for each particle.

The measured autofluorescence intensities and the backscatter values from the plurality of particles are processed to determine if a potential biohazard exists. At least one autofluorescence intensity value for each particle is provided to a pattern recognition classifier if a potential biohazard is present. The classifier is trained to recognize at least one variety of airborne particulate matter.

In accordance with another aspect of the present invention, a computer program product is provided for evaluating sensor data associated with airborne particular matter comprising a plurality of particles. The product includes sensor software that receives a measurement of the backscatter induced by each of the particles under a light source. This measurement is represented as a backscatter value for each particle. The sensor software also receives at least one autofluorescence intensity value for each of the particles reflecting the autofluorescence of the particle at least one characteristic wavelength.

The sensor then processes the measured autofluorescence intensity values and the backscatter values from the plurality of particles to determine if a potential biohazard exists. A pattern recognition classifier receives at least one of the autofluorescence intensity values from each of the plurality of particles. The pattern recognition classifier is trained to identify at least one variety of airborne particulate matter.

In accordance with yet another aspect of the present invention, a method of signal processing is disclosed wherein the signal represents plurality of discrete events, each event having an associated value. A region of interest comprising at least one range of values. Over a period of time, an average event ratio is determined. This ratio is equal to the number of events over the period of time with associated values within the at least one range of values comprising the region of interest to the number of events over the same time with associated values within at least one range of values not within the region of interest.

The signal representing the plurality of events is multiplied by a value equal to an instantaneous value for the number of events with associated values within the at least one range of values comprising the region of interest. This product is divided by the product of the average event ratio and an instantaneous value for the number of events with associated values within the at least one range of values not associated with the region of interest.

In accordance with still another aspect of the present invention, a computer program product, operative in a data processing system, is disclosed for processing a signal representing a plurality of discrete events, each event having an associated value. Sensor software defines a region of interest comprising at least one range of values. The software then determines over a period of time an average event ratio equal to the number of events with associated values within the at least one range of values comprising the region of interest to the number of events with associated values within at least one range of values not within the region of interest. The software then multiplies the signal representing the plurality of events by a value equal to an instantaneous value for the number of events with associated values within the at least one range of values comprising the region of interest. This product is divided by the product of the average event ratio and an instantaneous value for the number of events with associated values within the at least one range of values not associated with the region of interest.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

For the purpose of illustration, an example embodiment of the present invention is described as incorporated into conventional mail handling equipment. The mail handling equipment includes pinch points to facilitate the release of dry chemical agents, such as pathogens, that are contained within or on flat mail or letter mail articles. The system collects air samples of released particulates for analysis. An air sample is processed by subjecting the sample to ultraviolet (UV) light and measuring fluorescence and backscatter signals from the particles it contains. A second air sample is collected by a wet sampling device that converts the particulate into a liquid sample for forensic analysis. Upon detection by the biohazard sensor of a potential release of hazardous material, the wet sample is preserved for forensic analysis to confirm the presence of the hazardous substance.

The collectors within the system are installed downstream of a pinch point in the mail-handling equipment. A negative air pressure zone is maintained downstream of the air sample collection points, thereby drawing potentially contaminated air to particle sensors. Air drawn from the mail-handling equipment for analysis is filtered, for example by high efficiency particulate arresting (HEPA) filters, before being released back into the facility.

Air is drawn out of the mail handling equipment by a blower through a flexible duct. Separate pitot tubes in the flexible duct permit air to be drawn through tubing feeding at least one biosensor and a wet-sampling device. In the example embodiment, the biosensor is a BIONI™ System manufactured by Pacific Scientific Instruments. The biosensor monitors the air for counts of particulate matter. This occurs about once every second in the example embodiment. The wet sampling device continuously generates a liquid sample from the air, which is discharged to a vial when the workstation instructs. In the example embodiment, the wet sampling device is the Wet Sampler manufactured by Mesosystems. Airflow and mail sensors can be installed to provide monitoring of airflow and mail processing. Air is exhausted through a rough filter and a HEPA filter before being released back into the facility.

The biosensor monitors the particles under UV light and determines the particle size and the auto-fluorescence intensity. The data is sent via a local area network (LAN) to a workstation PC where data from the sensors are collected, analyzed, and displayed. An alarm condition is declared when the presence of a pathogen or other dangerous substance is indicated.

When the biosensor indicates a high probability that a hazardous substance is present in the sample, the sample is provided to a pattern recognition classifier that identifies the detected substance. The classifier uses the gathered data to check the substance against a number of substances that the classifier has been optimized to detect. These substances may include both pathogens and common hoax substances, such as talc or yeast. The classification result is provided to an operator to aid in evaluating the threat posed by the detected substance.

Figure 1:
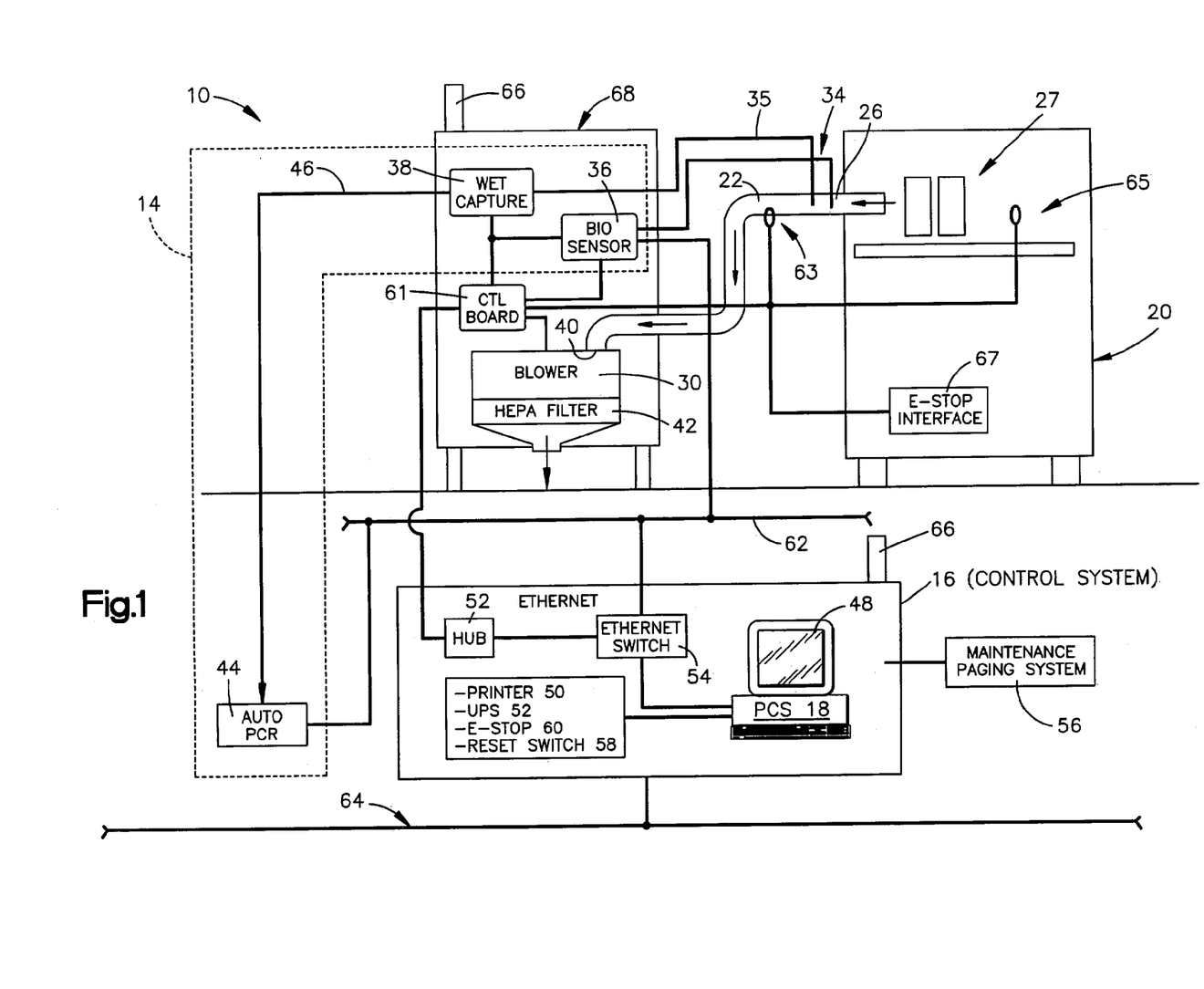
FIG. 1 is a schematic representation of an example embodiment of the present invention installed in conjunction with mail-handling equipment.

The pathogen identification system 10, implemented in the context of a mail handling system, includes an air handling system 12, a detection portion 14, a control system 16, and a particulate characterization software 18 to detect hazardous pathogens. In the example embodiment, these components are connected to and work in conjunction with conventional mail handling equipment 20. The characterization software 18 analyzes the output of the detection portion 14 using a pattern recognition classifier to increase the probability of accurate pathogen detection.

Now referring to FIG. 1, the air handling system 12 includes a flexible piece of round inlet duct 22 connected at a first end 24 to an orifice 26, approximately three inches in diameter, exiting the side of the conventional mail handling equipment 20 providing an air passageway downstream of a pinch point 27. The opposing second end 28 of the inlet duct is connected to a blower motor 30. The blower motor 30 draws air from the mail handling equipment 20 through the orifice 26 creating a negative air pressure at the inlets 32 of pitot tubes 34 installed through the inlet duct 22 along the interior walls 35. The inlets 32 of the pitot tubes 34 are aligned parallel with and opposing the air drawn from the mail handling equipment flow stream, such that the air samples are fed by feeding tubes 35 to a biosensor 36 and a wet sampler 38. The remaining air in the inlet duct 22 passes through a coarse pre-filter 40 positioned upstream of the blower motor 30 and is exhausted into the facility after being passed through a HEPA filter 42 for a final cleaning. An alternative approach to a single duct is to insert collection ducts at multiple locations along the mail handling equipment 20, including the shingler, stacker, and feeder portions of the machine.

The detection portion 14 includes the biosensor 36, a wet sampler 38, and a liquid medium collector 44. The liquid medium collector 44, which in the example embodiment is a Polymerase Chain Reaction (PCR) based DNA amplification system, is connected by a transfer tube 46 to the wet sampler 38 to process a liquid sample for a second tier confirmation of the biohazard. One embodiment uses a wet sampler manufactured by Mesosystems. The Mesosystems Wet Sampler 38 employs a streaming fluid approach, with no re-circulation, using a sample capture vial. The sample capture vial contains fluid processed during the time of the trigger event. This approach minimizes the inhibitors that may be present in the capture fluid, improving the accuracy of PCR based identification. Fluid containers are sized to accommodate the fluid collected during two full shifts of operation.

The control system 16, as shown in FIG. 1, includes a workstation PC 48 to implement communications with the air handling system 12, the detection portion 14, and facility personnel. All communication with the workstation PC 48 is preferably implemented using Ethernet and RS-485 serial communications. The control system 16 further includes a printer 50, a HUB 51, an uninterruptible power supply (UPS) 52, an Ethernet switch 54, a maintenance paging system 56, a reset switch 58, and an emergency stop (E-stop) 60. The HUB 51 responding to a RS-485 signal from a control board 61, routes signals between the workstation PC 48 and the biosensor 36, the wet sampler 38, and the liquid medium collector 44.

The control system 16 is fully networked to sensors and samplers through RS-485 serial communications to provide system graphics depicting all detection systems. The control board 61 links the control system 16 with system monitoring sensors and the mail handling equipment 20. An air flow sensor 63 mounted in the inlet duct 22 can monitor the airflow status and report out-of-tolerance fluctuations. Fluctuations may result from blower motor failure, filter clogging, and physical obstructions in the inlet duct 22 and tubing. A mail flow sensor 63 positioned in the mail handling equipment 20 monitors the flow of mail. An emergency stop interface 67 is connected to the power source or equivalent of the mail handling equipment 20 to shutdown the mail handling equipment when a potential bioagent has been detected or other system problems warrant investigation. The workstation PC 48 monitors the condition of the detection portion 14, the air handling system 12, and the control system 16.

In addition, the workstation PC 48 may be fully networked to a mail-processing facility through a site local area network 64 supporting auto-voice messages, automatic notification through a pager system, e-mail, or any other electronic communication. Using this network, upon detection of a potentially hazardous substance, the workstation PC can activate the wet sampler 38 to transfer a liquid medium containing a particulate sample to the liquid medium collector 44, send voice and e-mail messages to site authorities, and shut down the mail handling equipment 20.

The system 10 uses various methods to provide complete system diagnostics. The biosensor 36 monitors the status of key operating parameters including laser power, internal airflow rate, and internal counter board errors. These parameters can be reported over an Ethernet connection to the workstation PC 48. Likewise, the wet sampler 38 can report self-diagnostic information relating to its key components, which may include the status of a peristaltic pump, various fluid levels, and a make-up fan status.

In addition to monitoring, the workstation PC 48 can act on receipt of the self-diagnostic errors. When a problem is detected, the workstation PC 48 can automatically shut down the associated mail-handling equipment 20, flash one or more stack lights 66, and send a page over the maintenance paging system 56. Maintenance personnel can be provided information at the workstation PC 48 to help diagnose the problem and verify that the issue has been resolved. In addition, audible warnings can be provided on a cabinet 68 to indicate when the system is on-line and functioning properly.

Air samples that flow into the biosensor 36 and the wet sampler 38 can be filtered via one of two methods, using a conventional screen filter or a "scalper" filter. The screen filter may use four or more progressively finer screens housed in a compact enclosure. By way of example, the screen filter might include four screens with grid sizes of seven hundred and fifty microns, five hundred microns, two hundred and fifty microns, and one hundred microns. Generally, screen filters can last for several hours of operation before cleaning or replacement is required. Increasing the size of the screen filter reduces the frequency of required maintenance, but requires a corresponding increase in the size of the enclosure.

Figure 2:
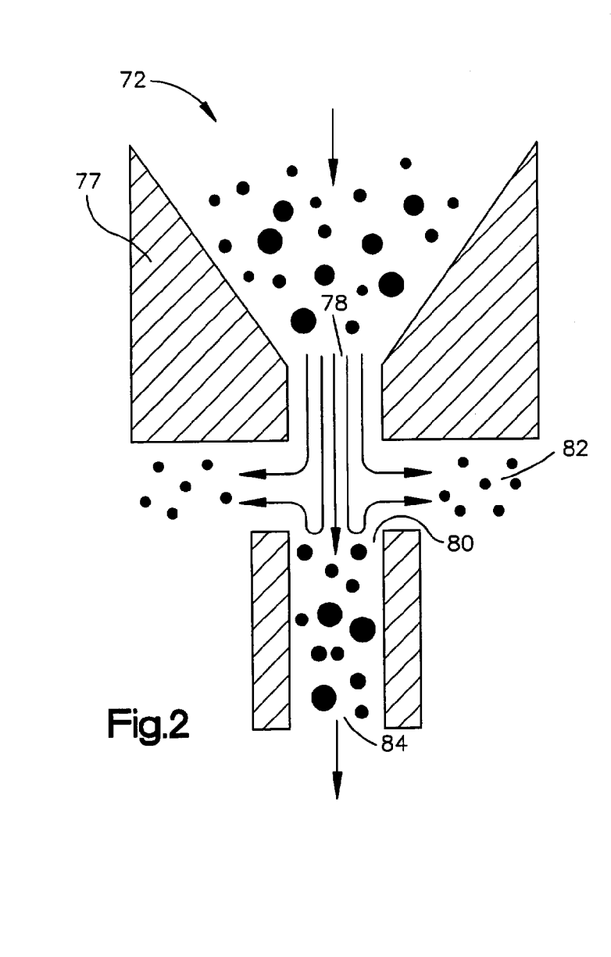
FIG. 2 is a partial cross section of a "scalper" filter.

An alternative to the screen filter is illustrated in FIG. 2. The scalper filter 72 can potentially eliminate the need for fine screen filters by exhausting particles of large size and delivering an airstream containing the particles of interest to downstream detection and collection. The scalper 72 comprises a virtual impactor 77 in which airborne particulates are separated according to size as illustrated in FIG. 2. Air is accelerated through a nozzle 78 towards a receiving probe 80 into which only a fraction of the air is permitted to enter, typically around ten percent. The air is able to bend and be exhausted out the major flow 82, but particles larger than a given size will have too much momentum to follow the air stream and become entrained in the minor flow 84. Smaller particles will follow the air and exhaust through the major flow. The "cut-size" of the virtual impactor 77, the particle size at which half of the particles enter the minor flow 84, is dependent on the design of the impactor and the flow rate of the air stream. Virtual impactors have traditionally been used to supply a concentrated stream (i.e. the major flow) of desired particles to a downstream sampler or other device for collection or analysis of the particles. This technique is used inside the biosensor 36 prior to introducing the air sample to the sensor view volume.

As a filter, the virtual impactor 77 diverts large, unwanted particles to the minor flow 84. The major flow 82, which includes the smaller, desirable particles, is delivered to downstream samplers or analysis devices. This approach can be used to filter the airflow prior to providing the air samples to the biosensor 36 and the wet sampler 38. This method can eliminate entirely the need for screen filters in these locations.

The biosensor 36 is a real-time detection mechanism to detect concentrated biological particulate in the mail-handling equipment 20. The system 10 continually samples the air in the mail handling equipment 20. The biosensor 36 provides fluorescence data that allows the system to detect the particulate matter present in the sampled air. Often, this will consist of non-hazardous contaminants, such as ordinary dust and paper fibers. The biosensor 36 can be, for example, a combination of a laser or LED based ultraviolet fluorescence particle counter and an aerosol concentrator such as the Pacific Scientific Instruments (PSI) BIONI™ system. Concentrated air samples are injected into a sampling chamber of the biosensor 36. The air samples are analyzed by an ultraviolet fluorescence particle counter to determine if a high concentration of particulates is present. The concentration is compared to threshold levels defined as to distinguish between a biological and non-biological event. By fluorescing the sample with the ultraviolet laser and determining the concentration of the sample that fluoresces at ultraviolet frequencies characteristic of NADH (Nicotinamide Adenine Dinucleotide) and/or Tryptophan, an accurate determination of the potential threat of the sample can be determined. This substantially reduces the number of false positives that would be generated if the system relied solely on a particulate count.

The wet sampler 38 is a real-time air particulate sampling and analysis mechanism continuously generating a liquid medium of the sampled air. In the example embodiment, the wet sampler 38 is a Mesosystems wet sampling system, which includes an aerosol concentrator and a discharge collection reservoir. The wet sampler 38 interfaces with the biosensor 36 to ensure the potential biological contaminant is captured in the liquid medium. An amount of sampled medium is stored for a period of time equal to at least the electro-mechanical time delay or hysteresis of the ultraviolet fluorescent particle counter before it is discarded into the discharge collection reservoir. If a potential biohazard event is detected, an alarm condition is declared and the wet sampler diverts the liquid medium into a collection vial of the liquid medium collector 44 for further analysis. If no potential biohazard event is detected, then the sample is discharged into the discharge collection system for later disposal.

Returning to the operation of the biosensor 36, the biosensor collects data both for determination of a threat condition and for identification of a detected substance. Some of these functions may be performed via one or more computer software program on the PC 48. In the example embodiment, the sensor control, signal processing, and pattern recognition functions are all performed via computer software.

To determine if a sample is likely to contain harmful biological material, the biosensor 36 provides at least two values for each detected particle. A backscatter value, which is indicative of particle size, is determined as well as at least one autofluorescence intensity value representing the autofluorescence intensity of the sample around a specific wavelength of interest. Two examples of these wavelengths of interest include the emission wavelengths of NADH and Tryptophan, approximately 360 nm and 440 nm respectively. In one embodiment of the invention, the measured autofluorescence and backscatter values are processed in raw form and provided directly to a neural network classifier. In an alternate embodiment, at least one of the autofluorescence intensity values is resolved with the particle size into a single combined metric using the backscatter signal.

Using this combined metric, the particles can be assigned values and associated with one of a plurality of ranges within a histogram. Each of these ranges will have an associated count equal to the number of particles associated with that range over a determined period. A region of interest encompassing at least one range within in the histogram is chosen to encompass values of the combined metric associated with the size and fluorescent properties of hazardous pathogens. This is referred to as the region of threat. These ranges are selected by an operator based upon the characteristics of known biohazards using configuration software for the biosensor 36. Once the region of threat is defined, sensor control software measures and tracks the particle counts in the region of threat.

In the present invention, the level of threat is determined by summing the total particle counts and comparing them to a user defined dynamic alarm level. The alarm level is determined by using a rolling average of the total counts to determine the background level. A margin is then added to this rolling average to yield a dynamic alarm level based on background conditions.

Threat discrimination is further improved using a selective signal amplification technique in order to emphasize particle counts that fall within the region of threat relative to particle counts falling outside of the region of threat. A flow diagram of an example embodiment of this process as it may be applied to a particle detection system is provided as FIG. 3. The details of the example below, such as the metric used in the analysis or the time periods chosen to establish particle counts, are included merely as examples and will change with the application for which the system is used. Other applications of this selective signal amplification process should be apparent to one skilled in the art in light of this example.

Figure 3:
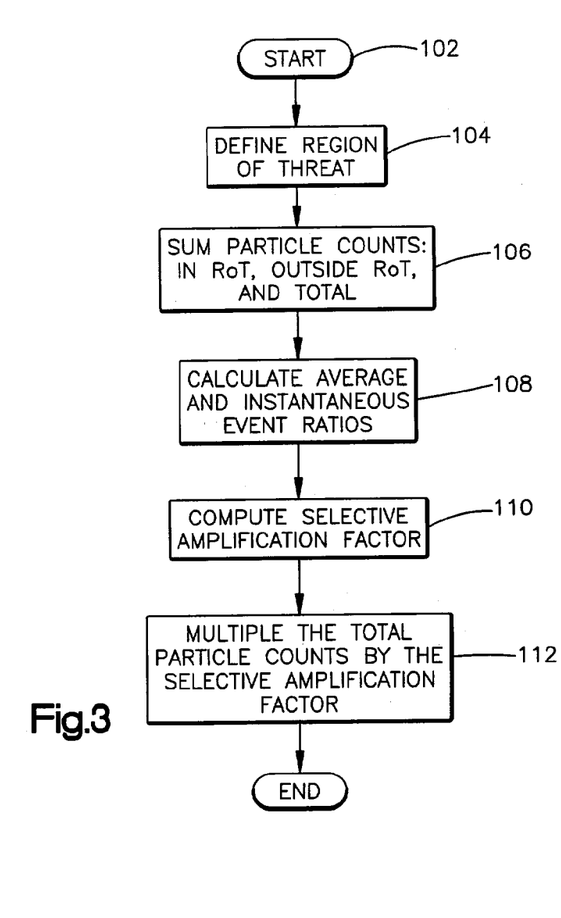
FIG. 3 is a flow diagram of a selective amplification process utilized within the present invention.

The process 100 begins at step 102. At step 104, at least one range of values for the combined metric is defined as a region of threat. The process continues to step 106, where the particle counts within the histogram are summed. A total sum of the particle counts over one second is computed, along with a count of the particles within the region of threat during that time, and a separate count for the particles outside of the region of threat. The process then continues to step 108, where two event ratios are computed, an average event ratio computed as a rolling average over a period of time and an instantaneous event ratio between the region of threat and the non-threat region. In the example embodiment, the rolling average is updated every second to reflect the sum of the particle counts over the past thirty seconds and the instantaneous ratio reflects the particle count over the last second. The average event ratio, $K_a$, and the instantaneous event ratio, $K_i$, are computed via the following formulas:

$$K_i = \frac{C_{RoT}}{C_{out}} \qquad \text{Equation 1}$$

$$\text{and}: K_a = \frac{\overline{C_{RoT}}}{\overline{C_{out}}} \qquad \text{Equation 2}$$

where $C_{RoT}$ is the instantaneous number of particle counts within the region of threat, $C_{out}$ is the instantaneous number of particle counts outside of the region of threat, and a bar over a value indicates a rolling average of the value in counts per second over the thirty second period.

The process then proceeds to step 110, where a selective amplification factor $K_{sa}$ is computed, such that:

$$K_{sa} = \frac{K_i}{K_a} \qquad \text{Equation 3}$$

At step 112, the summed particle counts are multiplied by the selective amplification factor. The amplification factor not only boosts the counts from events of interest, but also tends to attenuate those from events that are not of interest, reducing the chance of false alarms. This adjusted sum can be compared to an alarm level to determine if an alarm condition exists. The process then terminates at step 114.

Figure 4:
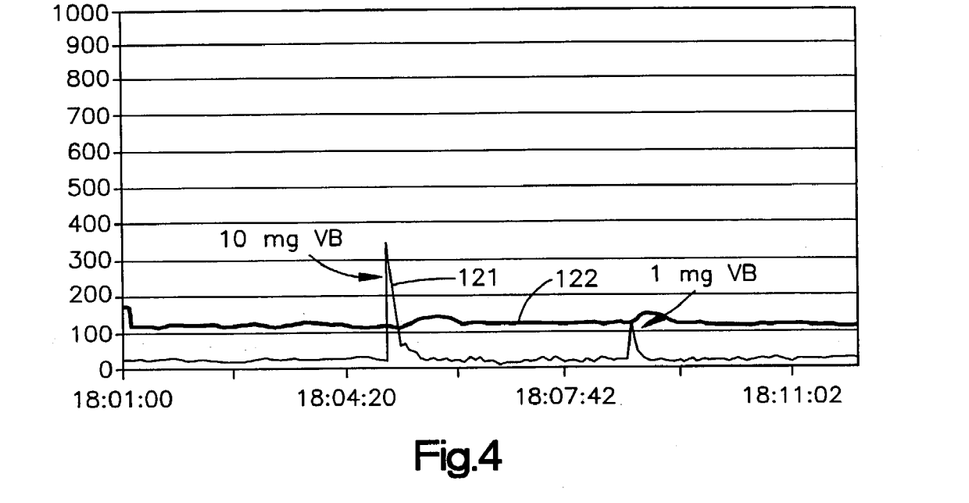
FIG. 4 is a chart comparing premeasured doses of Visiolite Blue, used as a simulant, to alarm thresholds in a prior art signal processing system.
Figure 5:
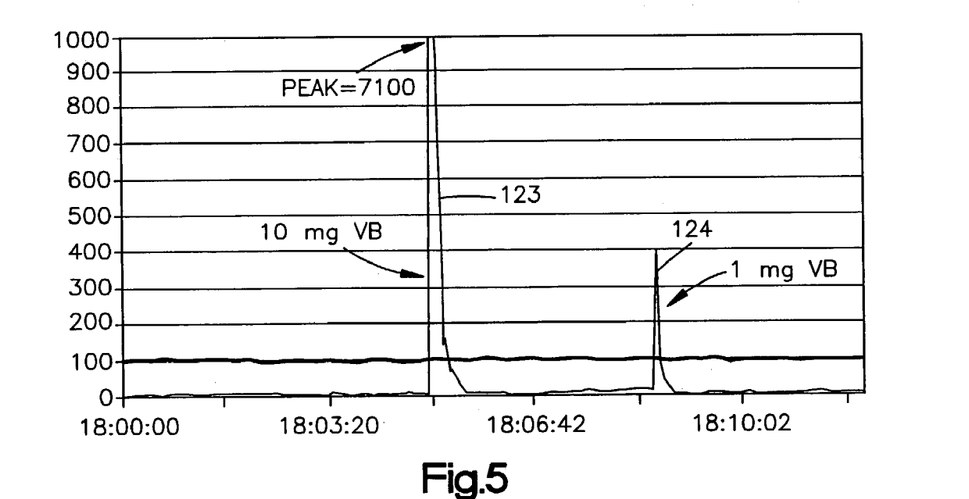
FIG. 5 is a chart comparing premeasured doses of Visiolite Blue to alarm thresholds in an example embodiment of the present invention.

Two samples of a simulant called Visiolite Blue (VB) measuring ten milligrams and one milligram were disposed in sealed envelopes. FIG. 4 shows the response 121 of a prior art biosensor against an alarm threshold 122. FIG. 5 illustrates a signal 123 processed in accordance with the present invention shown with an alarm threshold 124. Both charts were generated simultaneously using the same source data and test apparatus. As the charts illustrate, the signal processing of the present invention dramatically increases the signal level at the points where the simulant is introduced and reduces the background noise nearly to zero.

Figure 6:
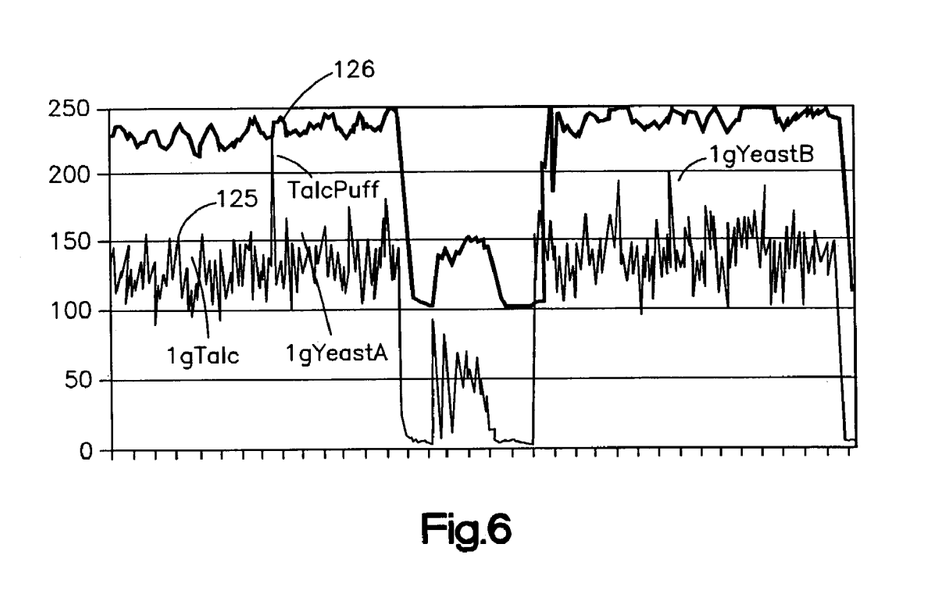
FIG. 6 is a chart comparing various substances to alarm thresholds in a prior art signal processing system.

Several hoax substances were tested using the signal processing technique of the present invention. A dense puff of powdered talc was injected into the input of the biosensor. The response of the prior art signal 125 processing technique against an alarm threshold 126 is shown in FIG. 6. As the figure illustrates, the talc puff was nearly successful in triggering an alarm condition in the prior art system. Small amounts (1 mg) of yeast introduced to the system, however, did not provoke a large response, despite the fact that yeast has fluorescence characteristics similar to that of *Bacillus globigii*, a relatively harmless substance with properties similar to anthrax.

Figure 7:
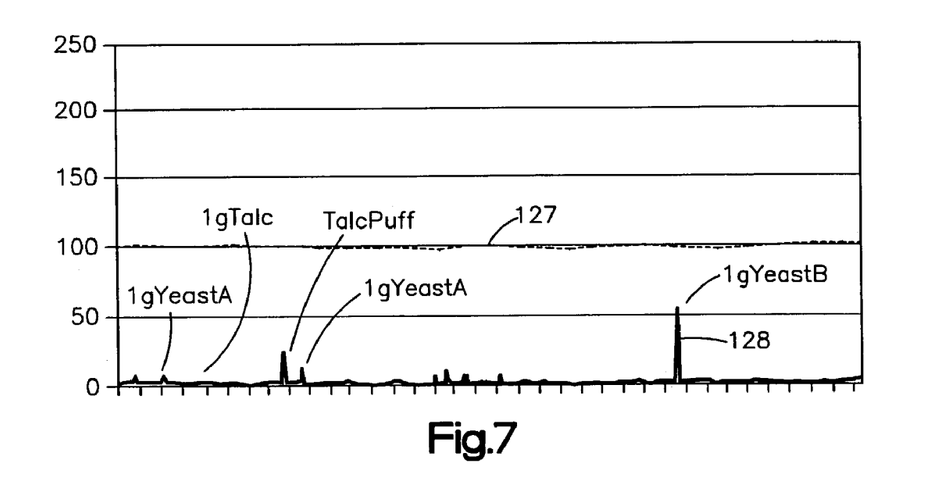
FIG. 7 is a chart comparing various substances to alarm thresholds using an example embodiment of the present invention

The response 127 of a system utilizing the signal processing method of the present invention is illustrated in FIG. 7 against an alarm threshold 128. As the figure demonstrates, the talc powder produced only a nominal response. The second puff of yeast produced a relatively large response, as might be expected, given the similarities in the autofluorescence properties of yeast and *Bacillus globigii*.

The substance identification function of the system identifies detected substances from their measured autofluorescence signals. The substance identification function can also be trained to utilize additional data, such as the measured backscatter signal, autofluorescence values associated with additional characteristic wavelengths, or similar quantifiable particle characteristics. To implement substance identification, a pattern recognition classifier is incorporated into the system 10. The classifier can be run at the workstation PC 48 or as a stand alone processing unit connected to the system via an Ethernet connection. Information gathered from the detected substance is provided directly to the classifier for immediate classification. In the example embodiment, the pattern recognition classifier is implemented as a generalized regression neural network simulated in a computer processor. Alternatively, a neural network could be implemented in hardware, as a plurality of parallel processing units. In another embodiment, the classifier could be implemented as a statistical classifier, using, for example, a least squared difference algorithm to determine an appropriate output class.

Regardless of the form it takes, the classifier is trained using numerous instances of the truth data for each of the selected substances. In addition, the classifier will be trained to distinguish paper dust, as such paper dust and fibers will be ubiquitous within a mail sorting system. This can be accomplished using measurements from a variety of paper dust samples.

As discussed above, in the example embodiment, the pattern recognition classifier takes the form of an artificial neural network classifier. An artificial neural network is composed of a large number of highly interconnected processing elements that have weighted connections. The organization and weights of the connections determine the output of the network, are optimized to reduce error and generate the best output classification.

Neural networks are good pattern recognition engines and robust classifiers, with the ability to generalize in making decisions about imprecise input data. Neural networks can provide solutions for a variety of classification problems such as speech, character, and signal recognition, as well as functional prediction and system modeling where the physical processes are not well understood or are highly complex. A neural network can accept distortions in the input data and can generalize to a solution if given incomplete data. Neural networks are good at solving problems that do not have an algorithmic solution or for which an algorithmic solution is too complex to be found. Neural networks are frequently well suited to problems which human beings are good at solving, but which are time-consuming or impossible for tradition automated methods.

Figure 8:
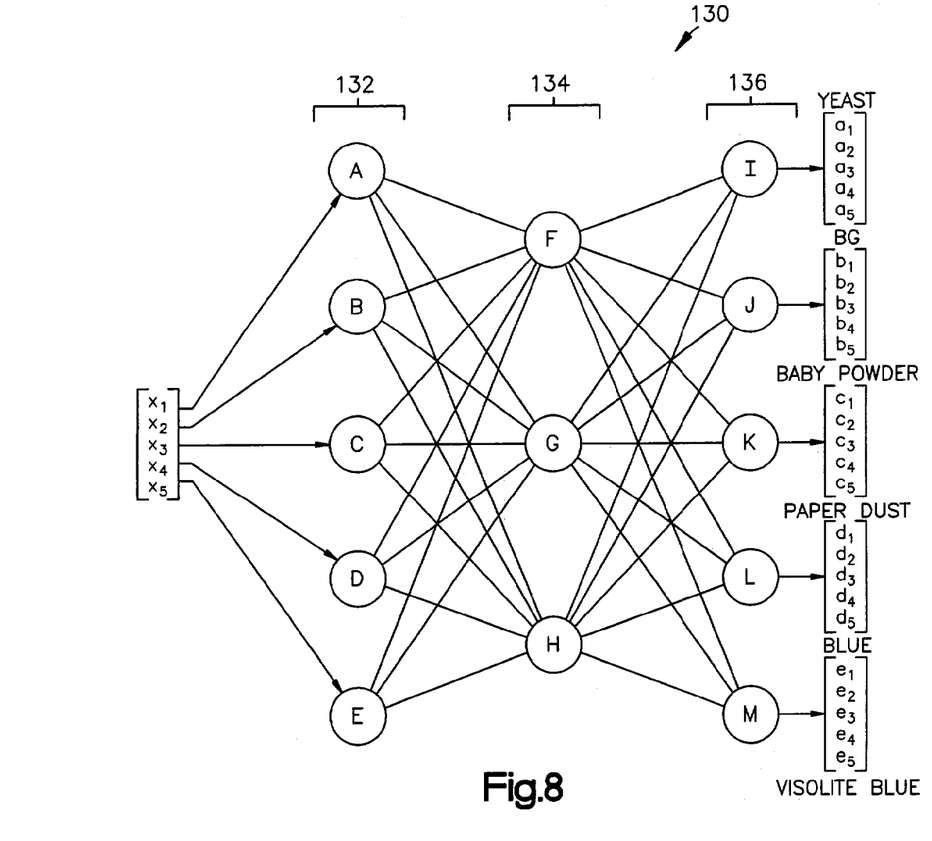
FIG. 8 illustrates an example neural network classifier.

FIG. 8 illustrates an example neural network classifier 130. The illustrated neural network is a three-layer back-propagation neural network suitable for use in an elementary pattern classifier. It should be noted here, that the neural network illustrated in FIG. 16 is a simple example solely for the purposes of illustration. Any non-trivial application involving a neural network, including pattern classification, would require a network with many more nodes in each layer and/or additional hidden layers.

In the illustrated example, an input layer 132 comprises five input nodes, A–E. A node, or neuron, is a processing unit of a neural network. A node may receive multiple inputs from prior layers which it processes according to an internal formula. The output of this processing may be provided to multiple other nodes in subsequent layers. The functioning of nodes within a neural network is designed to mimic the function of neurons within a human brain.

Each of the five input nodes A–E receives input signals with values relating to features of an input pattern. By way of example, the signal values could relate to the portion of an image within particular range of grayscale brightness. Alternatively, the signal values could relate to the average frequency of an audio signal over a particular segment of a recording. Preferably, a large number of input nodes will be used, receiving signal values derived from a variety of pattern features.

Each input node sends a signal to each of three intermediate nodes F–H in a hidden layer 134. The value represented by each signal will be based upon the value of the signal received at the input node. It will be appreciated, of course, that in practice, a classification neural network may have a number of hidden layers, depending on the nature of the classification task.

Each connection between nodes of different layers is characterized by an individual weight. These weights are established during the training of the neural network. The value of the signal provided to the hidden layer 134 by the input nodes A–E is derived by multiplying the value of the original input signal at the input node by the weight of the connection between the input node and the intermediate node (e.g., G). Thus, each intermediate node F–H receives a signal from each of the input nodes A–E, but due to the individualized weight of each connection, each intermediate node receives a signal of different value from each input node. For example, assume that the input signal at node A is of a value of 5 and the weights of the connections between node A and nodes F–H are 0.6, 0.2, and 0.4 respectively. The signals passed from node A to the intermediate nodes F–H will have values of 3, 1, and 2.

Each intermediate node F–H sums the weighted input signals it receives. This input sum may include a constant bias input at each node. The sum of the inputs is provided into a transfer function within the node to compute an output. A number of transfer functions can be used within a neural network of this type. By way of example, a threshold function may be used, where the node outputs a constant value when the summed inputs exceed a predetermined threshold. Alternatively, a linear or sigmoidal function may be used, passing the summed input signals or a sigmoidal transform of the value of the input sum to the nodes of the next layer.

Regardless of the transfer function used, the intermediate nodes F–H pass a signal with the computed output value to each of the nodes I–M of the output layer 136. An individual intermediate node (i.e. G) will send the same output signal to each of the output nodes I–M, but like the input values described above, the output signal value will be weighted differently at each individual connection. The weighted output signals from the intermediate nodes are summed to produce an output signal. Again, this sum may include a constant bias input.

Each output node represents an output class of the classifier. The value of the output signal produced at each output node is intended to represent the probability that a given input sample belongs to the associated class. In the example system, the class with the highest associated probability is selected, so long as the probability exceeds a predetermined threshold value. The value represented by the output signal is retained as a confidence value of the classification.

The example embodiment of the classifier of the present invention uses a neural network with an input layer of sixty-four elements, each corresponding to one of the series of autofluorescence signals. The number of nodes in the output layer will depend on the number of substances the network is trained to recognize. The network can be trained to rule out paper dust and known hoax powders as the source of an alarm condition. Various toxins may be added to the catalog of substance classifications as pathogen threats are identified. Further inputs, or features, may be included, such as autofluorescence signals associated with additional characteristic emission wavelengths or the backscatter signals.

Figure 9:
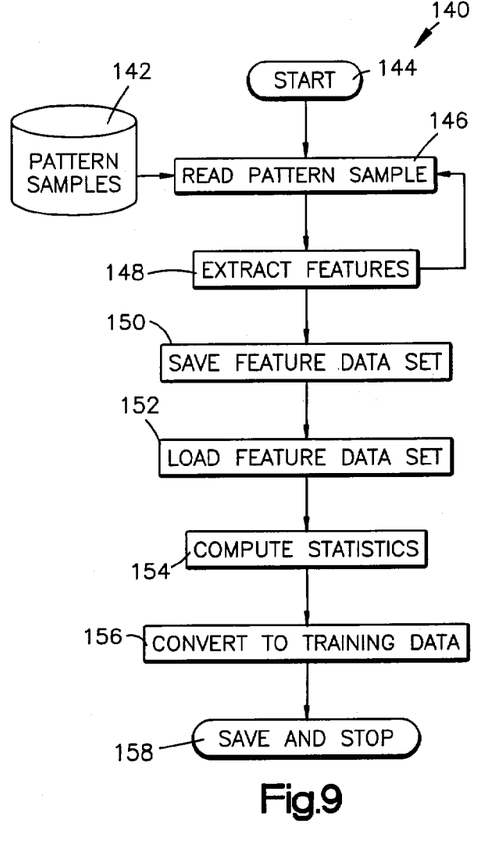
FIG. 9 is a flow diagram of the training of a pattern recognition classifier in accordance with one embodiment of the present invention.

FIG. 9 is a flow diagram illustrating the operation of a computer program 140 used to train a pattern recognition system via computer software. A number of pattern samples 142 are generated or collected from a population of real-world patterns. The number of pattern samples necessary for training varies with the application. The number of output classes, the selected features, and the nature of the classification technique used directly affect the number of samples needed for good results for a particular classifier. While the use of too few pattern samples can result in an improperly trained classifier, the use of too many samples can be equally problematic, as it can take too long to process the training data without a significant gain in performance.

The actual training process begins at step 144 and proceeds to step 146. At step 146, the program retrieves a pattern sample from memory. The process then proceeds to step 148, where the pattern sample is converted into a feature vector input describing the pattern sample as a vector of numerical measurement values. After each sample feature vector is extracted, the results are stored in memory, and the process returns to step 146. After all of the samples are analyzed, the process proceeds to step 150, where the feature vectors are saved to memory as a set.

The actual computation of the training data begins in step 152, where the saved feature vector set is loaded from memory. After retrieving the feature vector set, the process progresses to step 154. At step 154, the program calculates statistics, such as a mean and variance for the feature variables for each class, as well as a distance value in a defined feature space between each training vector of a class and the class mean. Intervariable statistics may also be calculated, such as a covariance matrix of the sample set for each class. The process then advances to step 156 where it uses the set of feature vectors to compute the training data. At this step in the example embodiment, a set of weights is calculated for the neural network that minimizes the mean squared error within a non-linear regression model. After these calculations are performed, the process proceeds to step 158 where the training parameters are stored in memory and the training process ends.

Figure 10:
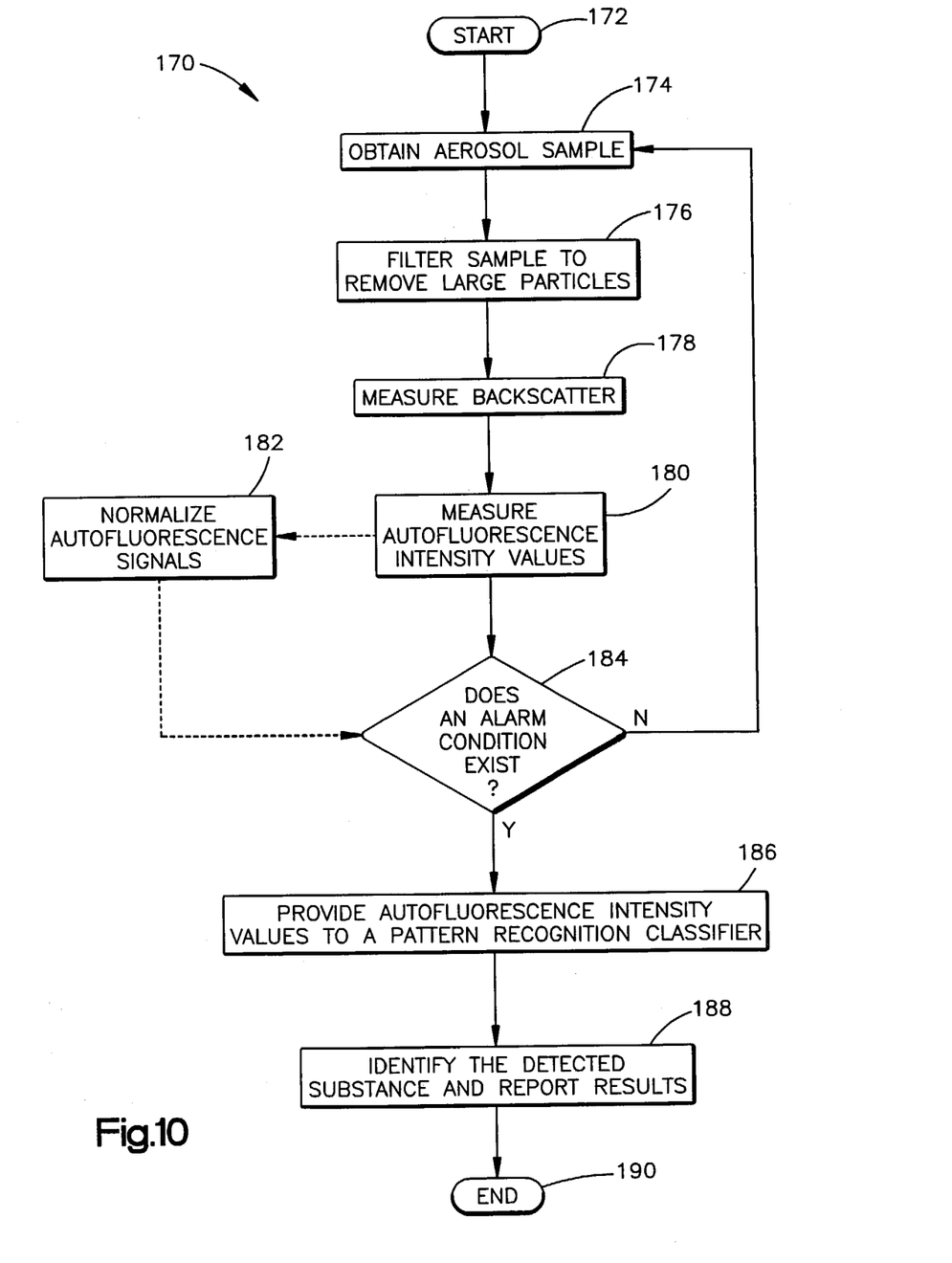
FIG. 10 is a flow diagram of the run-time operation of the operation of the pathogen identification system of the present invention.

FIG. 10 illustrates the run-time operation of the pathogen detection system 10 of the present invention. The process 170 begins at step 172. At step 174, the system obtains an aerosol sample for analysis. In the example embodiment of a mail processing system, this sample is taken from a mailed envelope. At step 176, the air sample is filtered to remove particles that are larger than a threshold size. In the example embodiment, particles larger than ten microns are filtered out.

At step 178, the size of the particles is determined by irradiating the aerosol sample with ultraviolet light and measuring the backscatter for each particle within the sample. This determined size is represented as a backscatter value. At step 180, the autofluorescence of the particles is measured at one or more characteristic wavelengths to obtain at least one autofluorescence intensity value for each particle. In the example embodiment, one intensity value is obtained. This value can represent the autofluorescence intensity of the particle at a characteristic point on the autofluorescence spectrum of NADH. The number of autofluorescence measurements as well as the characteristic wavelengths may be varied within the spirit of the invention. In addition, different frequencies of UV excitation may be used to evaluate the autofluorescence spectra of other substances that may be present with the particle such as Tryptophan.

Step 182 represents an alternative embodiment of the invention and is thus represented in broken lines in the flow diagram. At step 182, the one or more autofluorescence intensity values for each particle can be resolved into the determined backscatter value or one or more additional autofluorescence intensity values to form a combined metric. For example, this combined metric can incorporate the backscatter values into the autofluorescence intensity values as a normalization factor. Similarly, if two or more fluorescence intensity values are being measured for the embodiment, they can be resolved with each other to form a combined metric.

Regardless of whether the values are combined, the process then proceeds to step 184, where the autofluorescence and backscatter values are processed to determine if an alarm condition exists. In the example embodiment, this is accomplished by subjecting the total particle count to the selective amplification discussed earlier, and then determining if the particle count exceeds a dynamic threshold value. If an alarm condition is not found to exist, the system returns to step 174 to obtain another aerosol sample.

If an alarm condition exists, the process proceeds to step 186, where the autofluorescence intensity values for the particles are provided to a pattern recognition classifier. Autofluorescence values for other characteristic wavelengths, the backscatter values, or other particle properties can also be provided to the classifier. In one embodiment, the particles are sorted into predetermined ranges by their autofluorescence intensity values and their backscatter values to form multiple histograms. The quantity of particles falling within each range of the histograms provides features for the classifier. Where the autofluorescence signals have been normalized, the backscatter value is incorporated into the autofluorescence intensity values as a normalization factor, and it is unnecessary to create and evaluate a separate backscatter histogram. The process then proceeds to step 188 where the pattern recognition classifier identifies the detected substance and reports the classification result and a confidence value to an operator. The system may take other actions as well, such as sounding an audible alarm or shutting down the monitored system depending on the results. The process then ends at step 190.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A method for detecting airborne particular matter comprising a plurality of particles, comprising:
    measuring the backscatter induced by each of the particles under a light source to determine a backscatter value for each particle;
    measuring the autofluorescence intensity of each of the particles around at least one characteristic wavelength to obtain at least one autofluorescence intensity value for each particle;
    processing the measured autofluorescence intensities and the backscatter values from the plurality of particles to categorize the plurality of particles into at least two event categories, such that each category has an associated particle count;

determining a weighting factor from the associated particle counts of the at least two event categories;

applying the determined weighting factor to a total particle count to produce an adjusted particle count;

comparing the adjusted particle count to a threshold value to determine if a potential biohazard exists.

2. A method as set forth in claim 1, further comprising providing at least one autofluorescence intensity value to a pattern recognition classifier.

3. A method as set forth in claim 2, wherein the measured backscatter value for each particle is provided to the pattern recognition classifier.

4. A method as set forth in claim 3, wherein the step of providing the at least one autofluorescence value to the pattern recognition classifier includes resolving the backscatter value and at least one autofluorescence intensity value from each particle into a normalized metric and providing the normalized metrics from the plurality of particles to the pattern recognition classifier.

5. A method as set forth in claim 1, wherein determining the weighting factor comprises:

determining over a period of time an average event ratio equal to the number of particles associated with a first event category to the number of particles associated with a second event category; and determining the weighting factor as instantaneous value for the number of particles associated with the first category divided by the product of the average event ratio and an instantaneous value for the number of particles associated with the second category.

6. A method as set forth in claim 1, wherein one of the at least one characteristic wavelengths is associated with an autofluorescence emission spectrum of Tryptophan.

7. A method as set forth in claim 1, wherein one of the at least one characteristic wavelengths is associated with an autofluorescence emission spectrum of NADH.

8. A method as set forth in claim 1, wherein the particulate matter is sampled from air expelled from an envelope by mail processing equipment.

9. A method of signal processing wherein the signal represents plurality of discrete events, each event having an associated value, comprising:

defining a region of interest comprising at least one range of values;

determining over a period of time an average event ratio equal to the number of events with associated values within the at least one range of values comprising the region of interest to the number of events with associated values within at least one range of values not within the region of interest; and multiplying the signal representing the plurality of events by a value equal to an instantaneous value for the number of events with associated values within the at least one range of values comprising the region of interest divided by the product of the average event ratio and an instantaneous value for the number of events with associated values within the at least one range of values not associated with the region of interest.

10. A method as set forth in claim 9, wherein the each event represents a detected particle, the associated range of each event represents the backscatter and autofluorescence properties of the represented particle, and the region of interest is defined according to the backscatter and autofluorescence properties of common biological pathogens.

11. A computer program product, comprising a series of computer executable instructions embedded on a computer readable medium, for evaluating sensor data associated with airborne particular matter comprising a plurality of particles, the computer executable instructions comprising:

sensor software that receives a measurement of the backscatter induced by each of the particles under a light source, represented as a backscatter value for each particle, and at least one autofluorescence intensity values for each of the particles reflecting the autofluorescence of the particle at least one characteristic wavelength and comprising executable instructions operative to perform the following steps:

processing the measured autofluorescence intensity values and the backscatter values from the plurality of particles to categorize the plurality of particles into at least two event categories, such that each category has an associated particle count;

determining a weighting factor from the associated particle counts of the at least two event categories;

applying the determined weighting factor to a total particle count to produce an adjusted particle count; and comparing the adjusted particle count to a threshold value; and a pattern recognition classifier, trained to identify at least one variety of airborne particulate matter, that receives at least one autofluorescence intensity value from each of the plurality of particles.

12. A computer program product as set forth in claim 11, wherein the at least one characteristic wavelength is a plurality of characteristic wavelengths and the sensor software resolves at least two autofluorescence intensity values from each particle, each representing a different characteristic wavelength, into a normalized metric and the normalized metrics from the plurality of particles are received at the pattern recognition classifier.

13. A computer program product as set forth in claim 11, wherein the measured backscatter value from each particle is received at the pattern recognition classifier.

14. A computer program product as set forth in claim 13, wherein the sensor software resolves the backscatter value and at least one autofluorescence intensity value from each particle into a normalized metric and the normalized metrics from the plurality of particles are received at the pattern recognition classifier.

15. A computer program product as set forth in claim 11, wherein one of the at least one characteristic wavelengths is associated with an autofluorescence emission spectrum of Tryptophan.

16. A computer program product as set forth in claim 11, wherein one of the at least one characteristic wavelengths is associated with an autofluorescence emission spectrum of NADH.

17. A computer program product as set forth in claim 11, wherein the particulate matter is sampled from air expelled from an envelope by mail processing equipment.

18. A computer program product, comprising a series of computer executable instructions embedded on a computer readable medium, for processing a signal representing a plurality of discrete events, each event having an associated value, the computer executable instructions comprising:

sensor software that defines a region of interest comprising at least one range of values, determines over a period of time an average event ratio equal to the number of events with associated values within the at least one range of values comprising the region of interest to the number of events with associated values within at least one range of values not within the region of interest, and multiplies the signal representing the plurality of events by a value equal to an instantaneous value for the number of events with associated values within the at least one range of values comprising the region of interest divided by the product of the average event ratio and an instantaneous value for the number of events with associated values within the at least one range of values not associated with the region of interest.

19. A computer program product as set forth in claim 18, wherein the events each represent a detected particle, the associated range of each event represents the backscatter and autofluorescence properties of the represented particle, and the region of interest is defined according to the backscatter and autofluorescence properties of common biological pathogens.

* * * * *